US008658371B2

(12) United States Patent
Roepman et al.

(10) Patent No.: US 8,658,371 B2
(45) Date of Patent: Feb. 25, 2014

(54) MEANS AND METHOD FOR DETERMINING TUMOR CELL PERCENTAGE IN A SAMPLE

(75) Inventors: Paul Roepman, Utrecht (NL); Annuska Maria Glas, Assendelft (NL)

(73) Assignee: Agendia B.V., Amsterdam (NL)

( * ) Notice: Subject to any disclaimer, the term of this patent is extended or adjusted under 35 U.S.C. 154(b) by 193 days.

(21) Appl. No.: 13/061,286

(22) PCT Filed: Sep. 1, 2009

(86) PCT No.: PCT/NL2009/050519
§ 371 (c)(1),
(2), (4) Date: Apr. 8, 2011

(87) PCT Pub. No.: WO2010/024677
PCT Pub. Date: Mar. 4, 2010

(65) Prior Publication Data
US 2011/0269127 A1    Nov. 3, 2011

(30) Foreign Application Priority Data
Sep. 1, 2008  (EP) ..................................... 08163379

(51) Int. Cl.
*C12Q 1/68* (2006.01)
(52) U.S. Cl.
USPC ........................................ 435/6.14; 435/6.11
(58) Field of Classification Search
None
See application file for complete search history.

(56) References Cited

U.S. PATENT DOCUMENTS

2004/0053247 A1    3/2004    Cordon-Cardo et al.

FOREIGN PATENT DOCUMENTS

| WO | 02103320 A2 | 12/2002 |
| WO | 2004009618 A2 | 1/2004 |
| WO | 2004106375 A1 | 12/2004 |
| WO | 2005068622 A2 | 7/2005 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Bhattacharjee et al., "Classification of Human Lung Carcinomas by mRNA Expression Profiling Reveals Distinct Adenocarcinoma Subclasses", PNAS, vol. 98, No. 24, pp. 13790-13795; 2001.
XP-002513552; Database GEO, Online, "Agilent 012391 Whole Genome Oligo Microarray", retrieved from NCBI Database accession No. GPL1708 http://www.ncbi.nlm.nih.gov/geo/query/acc.cgi?acc=GPL1708; abstract; 2004.
Golub et al., "Molecular Classification of Cancer: Class Discovery and Class Prediction by Gene Expression Monitoring", Science, vol. 286, No. 5439, pp. 531-537; 1999.
Bertucci et al., "DNA Arrays in Clinical Oncology: Promises and Challenges", Laboratory Investigation, vol. 83, No. 3, pp. 305-316; 2003.
van 't Veer et al., "Gene Expression Profiling Predicts Clinical Outcome of Breast Cancer", Nature, vol. 415, pp. 530-536; 2002.
Furness et al., "International Variation in Histologic Grading is Large, and Persistent Feedback Does Not Improve Reproducibility", The American Journal of Surgical Pathology, vol. 27, No. 6, pp. 805-810; 2003.
Ross et al., "Standardizing Slide-Based Assays in Breast Cancer: Hormone Receptors, HER2, and Sentinel Lymph Nodes", Clinical Cancer Research, vol. 13, pp. 2831-2835; 2007.
Breen et al., "Circulating CD8 T Cells Show Increased Interferon-y mRNA Expression in HIV Infection", Cellular Immunology, vol. 178, pp. 91-98; 1997.
Eldering et al., "Expression Profiling via Novel Multiplex Assay Allows Rapid Assessment of Gene Regulation in Defined Signalling Pathways", Nucleic Acids Research, vol. 31, No. 23, pp. 1-9; 2003.
Baxevanis et al., "Antibody-Based Cancer Therapy", Expert Opinion on Drug Discovery, vol. 3, No. 4, pp. 441-452; 2008.
Wilcoxon et al., "Individual Comparisons by Ranking Methods", Biometrics Bulletin, vol. 1, No. 6, pp. 80-83; 1945.
Bauer et al., "Constructing Confidence Sets Using Rank Statistics", Journal of American Statistical Association, vol. 67, No. 339, pp. 687-690; 1972.

* cited by examiner

*Primary Examiner* — James Martinell
(74) *Attorney, Agent, or Firm* — Hoffmann & Baron, LLP

(57) ABSTRACT

The invention provides a method for determining the percentage of tumor cells in a sample of an individual, preferably a breast sample. More specifically, the invention provides one or more genes than can be used to determine the percentage of tumor cells. The invention further provides a set of probes, a set of primers, and uses thereof for detection of said one or more genes.

15 Claims, 9 Drawing Sheets

# MEANS AND METHOD FOR DETERMINING TUMOR CELL PERCENTAGE IN A SAMPLE

CLAIM OF PRIORITY

This application is the U.S. National Phase of, and Applicants claim priority from, International Application Number PCT/NL2009/050519 filed 1 Sep. 2009 and European Patent Application No. 08163379.4 filed 1 Sep. 2008, which are incorporated herein by reference.

BACKGROUND OF THE INVENTION

Incorporation of Sequence Listing

Incorporated herein by reference in its entirety is the Sequence Listing for the above-identified Application. The Sequence Listing is disclosed on a computer-readable ASCII text file titled "SequenceListing294-396PCTUS.txt", created on May 13, 2011. The sequence.txt file is 5.34 KB.

The invention relates to the field of tumor diagnostics, more specifically to new and alternative means and methods to determine the percentage of tumor cells in a sample. The invention allows the determination of the percentage of tumor cells based on the expression levels of a specific set of genes. The methods and means of the invention can be used in addition to a histopathological review of a sample and are particularly suited for determining the tumor percentage in samples that are too small or not suited for histopathological review.

Microarray diagnostics of sectioned primary tumor specimens is based on gene expression measurement of a specific set of predictive or prognostic genes. Commonly, bulk tumor samples are used for diagnostics that consist of tumor cells but also of surrounding stromal tissue. Although tumor stroma likely plays an important role in tumor development and metastasis, gene expression profiles are typically generated using tumor tissues that contain sufficient tumor cells. For example, the prognostic mammaprint 70-gene profile has originally been identified using samples with at least 50% tumor cells (van 't Veer et al., 2002. Nature 415: 530-536). If a sufficient tumor cell percentage is not reached, a tumor specimen will be disregarded from analysis.

Generally, tumor cell percentage assessment is performed by a pathologist who uses staining such as heamatoxilin-eosine (HE) staining for histopathological analyses of a sample. However, despite high pathological skills, histopathological tumor scoring remains a subjective and time consuming practise and can lead to inconclusive results (Furness et al., 2003. Am J Surg Pathol 27: 805-810; Ross et al, 2007. Clin Cancer Res 13: 2831-2835] including tumor cell percentage scoring (FIG. 1). In addition, pathological tumor cell scoring is impossible for samples that are too small or unsuited for histopathological analysis such as core biopsies and fine-needle aspirates.

Therefore, there is a need for a tumor percentage scoring method that can be used in addition to, or in stead of, histopathological analyses.

DESCRIPTION OF THE INVENTION

The invention provides a method for determining the percentage of tumor cells in a cell sample of an individual, the method comprising preparing an RNA sample from a cell sample from said individual, said cell sample comprising tumor cells or suspected to comprise tumor cells; determining RNA expression levels for a set of genes in said RNA sample; and determining the percentage of tumor cells in said cell sample on the basis of the levels of RNA determined for the set of genes, whereby the set of genes comprises at least one of the genes listed in Table 1. It is preferred that said at least one gene selected from Table 1 is selected from genes with SEQ ID NO 3 and SEQ ID NO 14.

Said method allows determining a tumor cell percentage (TCP) of a cell sample, which is a measure for the amount of tumor cells relative to the total amount of cells in said cell sample. This determination complements or replaces a histopathological determination. Only samples with a sufficient TCP can be used for subsequent expensive and time consuming analyses such as microarray-based prognostics, which will save time and money.

A method of the invention will further improve the efficiency and throughput as it does not require histo-pathological analysis for initial tumor percentage scoring. In addition, a method of the invention allows transcriptional diagnostics of small clinical samples, such as fine-needle aspirates.

A preferred method of the invention allows the discrimination between a sample comprising a specific minimal percentage of tumor cells, and a sample that scores below the minimal percentage, such as the discrimination between a sample comprising at least fifty percent tumor cells (TCP≥50), and a sample comprising less than 50 percent tumor cells (TCP<50). A more preferred method of the invention allows the discrimination between a sample comprising at least thirty percent tumor cells (TCP≥30), and a sample comprising less than 30 percent tumor cells (TCP<30).

Said sample can be any sample that can be obtained from a patient that suffers from, or is expected to suffer from, a tumor. Tumor, as used in this application is defined as a benign or, preferred, malignant neoplasia (cancer). A most preferred cancer is a breast cancer such as, but not limited to, ductal carcinoma and lobular carcinoma.

Therefore, a preferred sample for a determination of the percentage of tumor cells according to the invention is breast tissue, comprising a breast tumor or suspected of suffering there from.

A preferred sample is a biopsy. It is preferred that the biopsies have a depth of at most 10 millimeter, more preferred at most 5 millimeter, and a diameter of about 2 millimeter, about 3 millimeter, about 4 millimeter, about 5 millimeter, about 6 millimeter, about 7 millimeter, about 8 millimeter, about 9 millimeter, or about 10 millimeter. However, other forms that are equal in volume are also possible.

A further preferred sample is prepared from a needle aspiration biopsy, which is a procedure by which a thin needle is inserted in a tissue to extract cells.

A sample can be processed in numerous ways, as is known to a skilled person. For example, they can be freshly prepared from cells or tissues at the moment of harvesting, or they can be prepared from surgical biopsies that are stored at −70° C. until processed for sample preparation. Alternatively, tissues or surgical biopsies can be stored under protective conditions that preserve the quality of the RNA. Examples of these preservative conditions are fixation using e.g. formaline, RNase inhibitors such as RNAsin (Pharmingen) RNAlater (Ambion) or RNasecure (Ambion). Alternatively, specific salts such as a salt comprising ammonium sulfate or cesium sulphate can be added to the sample as an RNA-preserving agent.

RNA can be prepared from the fresh, frozen or preserved sample using known methods and means. Cellular disruption preferably takes place in a strong denaturant solution comprising guanidinium isothiocyanate, lithium chloride, sodium dodecylsulphate, and/or phenol. Total RNA is subsequently isolated by one of several methods including alcohol or LiCl precipitation, ultracentrifugation for example through cesium chloride, phenol-chloroform extraction or alternatives therefore known in the art, or by absorption to an affinity matrix, such as for example silica- or glass-based matrices or filters, or any combination thereof.

Messenger RNA (mRNA) is isolated using affinity chromatography to immobilized oligo(dT) or oligo(dU), or by specific removal of ribosomal RNA. If required, cDNA can be generated from total RNA or mRNA using one or more specific primers such as an oligod(T)-based primer, and/or random primers such as hexamer primers and nonamer primers.

The percentage of tumour cells in a method of the invention is determined on the basis of RNA levels determined for a set of genes comprising at least two of the genes listed in Table 1.

RNA levels can be determined by any method known to a skilled person, including but not limited to Northern blotting, dot blot analysis, quantitative PCR, RNase protection analysis, branched-DNA technology (Breen et al. (1997) Cell Immunol 178:91-98), and microarray analysis.

A preferred method is provided by microarray analyses, involving the use of selected biomolecules that are immobilized on a surface. A microarray usually comprises nucleic acid molecules, termed probes, which are able to hybridize to nucleic acid expression products. The probes are exposed to labeled sample nucleic acid, hybridized, and the abundance of nucleic acid expression products in the sample that are complementary to a probe is determined. The probes on a microarray may comprise DNA sequences, RNA sequences, or copolymer sequences of DNA and RNA. The probes may also comprise DNA and/or RNA analogues such as, for example, nucleotide analogues or peptide nucleic acid molecules (PNA), or combinations thereof. The sequences of the probes may be full or partial fragments of genomic DNA. The probe sequences are preferably synthetic nucleotide sequences, such as synthetic oligonucleotide sequences.

A further preferred method is provided by quantitative Polymerase Chain Reaction (qPCR). qPCR is performed by end-point measurements, in which the amount of a final product is determined, or preferably by real-time PCR (rtPCR), in which the amount of product is monitored during the reaction.

As is known to a skilled person, rtPCR can be performed either by the use of a nucleic acid intercalator, such as for example ethidium bromide or an other intercalating fluorescent dye such as, for example, CyberGreen, which interacts with double stranded products that are generated in the process resulting in an increase in fluorescence during amplification, or by the use of labeled probes that react specifically with the generated double stranded product of the gene of interest. Alternative detection methods that can be used are provided by dendrimer signal amplification, hybridization signal amplification, and molecular beacons.

Different amplification methods are known to a skilled artisan and can be employed for qPCR, including but not limited to classical PCR employing a reverse transcriptase and a DNA polymerase, rolling circle amplification, nucleic acid sequence-based amplification, transcription mediated amplification, and linear RNA amplification.

It is preferred that multiple nucleic acid gene expression products can be detected simultaneously. Therefore, methods such as reverse transcriptase-multiplex ligation-dependent amplification, which accurately quantifies multiple transcripts of interest in a one-tube assay (Eldering et al., Nucleic Acids Res 2003; 31: e153), and rtPCR amplification in a multiwell format, are preferred.

It is further preferred that the set of genes according to the invention comprises at least two of the genes listed in Table 1, more preferred at least three of the genes listed in Table 1, more preferred at least four of the genes listed in Table 1, more preferred at least five of the genes listed in Table 1, more preferred at least six of the genes listed in Table 1, more preferred at least seven of the genes listed in Table 1, more preferred at least eight of the genes listed in Table 1, more preferred at least nine of the genes listed in Table 1, more preferred at least ten of the genes listed in Table 1, more preferred at least eleven of the genes listed in Table 1, more preferred at least twelve of the genes listed in Table 1, more preferred at least thirteen of the genes listed in Table 1, more preferred at least fourteen of the genes listed in Table 1, more preferred at least fifteen of the genes listed in Table 1, more preferred at least sixteen of the genes listed in Table 1, more preferred at least seventeen of the genes listed in Table 1, more preferred at least eighteen of the genes listed in Table 1, more preferred at least nineteen of the genes listed in Table 1, more preferred at least twenty of the genes listed in Table 1, more preferred at least twenty five of the genes listed in Table 1, more preferred at least thirty of the genes listed in Table 1, more preferred all of the genes listed in Table 1.

It is further preferred that a set of genes according to the invention comprising at least two of the genes listed in Table 1 is randomly selected from the genes listed in Table 1.

It is further preferred that a set of genes according to the invention comprising at least two of the genes listed in Table 1 comprises genes that are ranked number 1 and 2, as indicated in Table 1, which genes are identified by SEQ ID NO 3 and SEQ ID NO 14.

Cross validation (CV) was used to rank order genes according to their CV performance. The rank order of a gene therefore, as provided in Table 1, is a measure for the correlation with pathologically determined TCP across the tumor samples of a gene. A gene with the highest correlation was put at position 1 (rank-ordered positions are provided in column entitled "Rank" of Table 1).

More preferred is a set of genes according to the invention comprising at least thirteen of the genes listed in Table 1 which are randomly selected from the genes listed in Table 1. More preferred is a set of at least thirteen genes that are ranked 1-13 and comprises all genes identified by SEQ ID NO: 1, SEQ ID NO: 2, SEQ ID NO: 3, SEQ ID NO: 9, SEQ ID NO: 13, SEQ ID NO: 14, SEQ ID NO: 15, SEQ ID NO: 20, SEQ ID NO: 23, SEQ ID NO: 24, SEQ ID NO: 25, SEQ ID NO: 28, and SEQ ID NO: 31, as indicated in Table 1.

Even more preferred is a set of at least thirteen genes that comprises genes identified by SEQ ID NO: 1; SEQ ID NO: 2, SEQ ID NO: 3, SEQ ID NO: 5, SEQ ID NO: 9, SEQ ID NO: 14, SEQ ID NO: 16, SEQ ID NO: 18, SEQ ID NO: 24, SEQ ID NO: 25, SEQ ID NO: 30, SEQ ID NO: 32, and SEQ ID NO: 33.

The level of expression of all genes in said set of thirteen stably expressed genes are all dependent of the percentage of tumor cells in the samples, and is increased if a sample with a higher tumor cell percentage. This 13-gene classifier constitutes a robust tumor cell percentage expression profile with a high performance resulting in an accurate classification of a sample with a low tumor cell percentage (TCP<30) and an accurate classification a sample with a high tumor cell percentage (TCP≥30).

The level of expression of a gene in a sample is preferably normalized to correct for difference between different samples and for correcting example systemic bias. Normalization can be performed by correcting the level of expression of a gene in a sample for the level of expression of one or more control genes in the sample. The control genes are selected on the basis that their level of expression hardly differs between samples from different individuals. Control genes that are often used for normalizing RNA expression data are housekeeping genes such as, for example, ribosomalRNA, glyceraldehyde 3-phosphate dehydrogenase, and beta-actin. Further known housekeeping genes include human acidic ribosomal protein, cyclophylin, phosphoglycerokinase, β2-microglobulin, β-glucuronidase, hypoxanthine phosphoribosyltransferase, transcription factor IID TATA binding protein, and transferrin receptor.

Therefore, a preferred method of the invention comprises normalizing the determined RNA levels of the set of genes in the sample.

A set of control genes that can be used for normalizing expression data such as microarray-based expression data and which are especially suited for breast sample was recently published (WO08039071A1), which reference is herein included by reference.

A preferred set of control genes for normalizing RNA expression data comprises calcium channel, voltage-dependent, gamma subunit 5 (CACNG5; NM_014404). More preferred is a set of control genes comprising CACNG5 and CAAX box 1 (CXX1, NM003928). More preferred is a set of control genes comprising CACNG5, CXX1 and killer cell immunoglobulin-like receptor, three domains, long cytoplasmic tail 1 (KIR3DL1, NM_013289). More preferred is a set of control genes comprising CACNG5, CXX1, KIR3DL1, and glycosylphosphatidylinositol specific phospholipase D1 (GPLD1, NM_001503). More preferred is a set of control genes comprising CACNG5, CXX1, KIR3DL1, GPLD1, and carbonic anhydrase (CA1, NM_001738).

The invention also provides a set of probes for determining the percentage of tumor cells in a sample of an individual, whereby said set of probes comprises probes specific for at least one of the genes listed in Table 1.

A probe preferably comprises a sequence of between 18 and 100 nucleotides that can basepair with an RNA expression product or derivative thereof of a gene listed in Table 1. A more preferred probe comprises between 25 and 80 nucleotides, more preferred about 60 nucleotides. It will be understood by a skilled person that the term "nucleotide" includes a ribonucleic acid residue, a desoxyribonucleic acid residue, a modified and/or chemically altered nucleid acid residue such as a locked nucleic acid and a peptide nucleic acid, and any combination thereof.

A preferred set of probes according to the invention comprises probes that are specific for genes identified by SEQ ID NO 3 and SEQ ID NO 14. The genes identified by SEQ ID NO 3 and SEQ ID NO 14 genes have the highest rank order and are therefore especially suited for determining a tumor cell percentage in a sample.

A further preferred set of probes according the invention comprises probes specific for at least thirteen of the genes listed in Table 1, whereby it is preferred that the set of probes comprises probes specific for genes identified by SEQ ID NO: 1; SEQ ID NO: 2, SEQ ID NO: 3, SEQ ID NO: 5, SEQ ID NO: 9, SEQ ID NO: 14, SEQ ID NO: 16, SEQ ID NO: 18, SEQ ID NO: 24, SEQ ID NO: 25, SEQ ID NO: 30, SEQ ID NO: 32, and SEQ ID NO: 33.

It is furthermore preferred that said set of probes is present on an array, preferably a microarray. In a preferred embodiment, said microarray further comprises a set of control genes that can be used for normalizing expression data. It is furthermore preferred that said microarray comprises not more than 10.000 probes, more preferred not more than 5000 probes, most preferred not more than 1000 probes, such as, for example, 100 probes or 500 probes.

The invention also provides the use of a set of probes according to the invention for determining the percentage of tumor cells in a sample of an individual, whereby it is further preferred that the individual is suffering from a breast tumor or suspected of suffering there from.

The invention also provides a set of primer pairs for determining the percentage of tumor cells in a sample of an individual, whereby said set of primer pairs comprises primer pairs specific for at least one of the genes listed in Table 1.

A primer comprises a short stretch of nucleotide residues that can basepair with an RNA expression product or derivative thereof of a gene listed in Table 1. The term primer pair refers to two primers that can basepair with an RNA expression product or derivative thereof of one gene. It is preferred that the two primers of a primer pair hybridize to different positions on an RNA expression product or derivative thereof to form double stranded sequences that can be used as a starting site for a polymerase to synthesize a double stranded product that is complementary to at least a part of the RNA expression product or derivative thereof. Repeating the procedure will result in the amplification of the double stranded product. The short stretch of nucleotide residues of a primer determines the specificity of the base pairing between a primer and the complementary RNA expression product or derivative thereof.

Factors that influence the base pairing comprise the number of nucleotide residues, the GC content, the nucleotide residues of the last 5 residues at the ends, and the possibility for primer hairpin formation. A preferred primer comprises between 15 and 50 nucleotide residues, more preferred between 16 and 30 residues, more preferred between 18 and 25 residues, such as 18 residues, 19 residues, 20 residues, 21 residues, 22 residues, 23 residues, 24 residues, or 25 residues. The most preferred number of nucleotide residues will be determined by the individual nucleotide residues.

A primer pair preferably can be used to obtain an indication of the RNA expression level of the set of genes in the sample by quantitative amplification. The amount of double stranded product that is formed during quantitative amplification can be determined fluorescent dyes that can intercalate into double stranded products. Alternatively, a molecular beacon comprising a fluorophore on one end and a quenching dye on the opposite end, can be employed that binds to the amplified target resulting in a fluorescent signal that is proportional to the amount of double stranded product.

A preferred set of primer pairs comprises primer pairs specific for at least two of the genes listed in Table 1.

A more preferred set of primer pairs comprises primer pairs that are specific for genes identified by SEQ ID NO 3 and SEQ ID NO 14.

An even more preferred set of primer pairs according comprises primer pairs that are specific for specific for genes identified by SEQ ID NO: 1; SEQ ID NO: 2, SEQ ID NO: 3, SEQ ID NO: 5, SEQ ID NO: 9, SEQ ID NO: 14, SEQ ID NO: 16, SEQ ID NO: 18, SEQ ID NO: 24, SEQ ID NO: 25, SEQ ID NO: 30, SEQ ID NO: 32, and SEQ ID NO: 33.

The invention also provides the use of a set of primer pairs according to the invention for determining the percentage of tumor cells in a sample of an individual, whereby it is further preferred that the individual is suffering from a breast tumor or suspected of suffering there from.

The invention further provides a kit for determining the percentage of tumor cells in a sample of an individual, the kit comprising methods and means for determining the level of expression of at least two genes in the sample. Said methods and means comprise a polymerase, such as a temperature-stable DNA-dependent DNA polymerase, and a reaction buffer that provides preferred conditions such as salt concentration and pH for the amplification reaction. The methods and means may further comprise an intercalating fluorescent dye or a molecular beacon that is specific for detection of the product of the set of at least two genes.

A preferred kit according to the invention comprises primer pairs that allow quantitative amplification of the set of at least two genes of the genes listed in Table 1 in the sample.

The invention also provides the use of a kit according the invention for determining the percentage of tumor cells in a sample of an individual, whereby it is preferred that the individual is suffering from a breast tumor or suspected of suffering there from.

The invention also provides a method of determining a percentage of tumor cells in a sample from an individual suffering from a tumor, or suspected of suffering from a tumor, the method comprising classifying a sample as derived from an individual having a tumor cell percentage below or above a defined threshold by a method comprising determining a level of RNA for a set of genes comprising at least one of the genes listed in Table 1 in a sample from said individual, whereby said sample comprises tumor cells or is suspected to comprises tumor cells, determining a similarity value for the level of RNA in the sample and a level of RNA for the set of genes in a patient having no tumor cells, and classifying the sample as having a tumor cell percentage above the threshold if said similarity value is below a first similarity threshold value, and classifying said sample as having a tumor cell percentage below the threshold if said similarity value exceeds said first similarity threshold value.

Said defined threshold is a measure for the percentage of tumor cells in a cell sample relative to the total amount of cells in said cell sample. Said defined threshold preferably is 80%, more preferred 70%, more preferred 60%, more preferred 50%, more preferred 40%, more preferred 30%, more preferred 20%, more preferred 10%. A most preferred threshold is 30%, whereby 30% of the total amount of cells comprises tumour cells.

It is furthermore preferred that the individual is suffering from a breast tumor or suspected of suffering there from.

In a preferred method of the invention, the set of genes comprises SEQ ID NO 3 and SEQ ID NO 14. A further preferred the set of genes comprises SEQ ID NO: 1; SEQ ID NO: 2, SEQ ID NO: 3, SEQ ID NO: 5, SEQ ID NO: 9, SEQ ID NO: 14, SEQ ID NO: 16, SEQ ID NO: 18, SEQ ID NO: 24, SEQ ID NO: 25, SEQ ID NO: 30, SEQ ID NO: 32, and SEQ ID NO: 33.

A method for determining a percentage of tumor cells in a cell sample from an individual suffering from a tumor, or suspected of suffering from a tumor, can be used in a method for classifying said cell sample, for example as provided by WO02103320, which is hereby incorporated by reference. The percentage of tumor cells is used for subtyping said cell sample on the basis of the determined tumor cell percentage. Cell samples can be subtyped as comprising, for example, tumor cell percentages of between 10 and 30%, of between 30 and 50%, of between 50 and 70%, and above 70%. A specific set of at least 5 classifying markers for each subtype is subsequently selected from the markers identified in any of Tables 1-6 of WO02103320, and used for classifying said cell sample.

In a further aspect, the invention provides the use of at least one of the genes listed in Table 1 as a tumor marker. A preferred gene is selected from SEQ ID NO: 7 (AQP1 aquaporin 1); SEQ ID NO: 17 (JAM2; junctional adhesion molecule 2); SEQ ID NO: 20 (LY75; lymphocyte antigen 75); SEQ ID NO: 23 (NTRK2 neurotrophic tyrosine kinase, receptor, type 2); SEQ ID NO: 28 (SCN4B sodium channel, voltage-gated, type IV, beta); and SEQ ID NO: 29 (SFRP1 secreted frizzled-related protein 1).

In yet a further aspect, the invention provides an antibody against one of more of the genes selected from SEQ ID NO: 7 (AQP1 aquaporin 1); SEQ ID NO: 17 (JAM2; junctional adhesion molecule 2); SEQ ID NO: 20 (LY75; lymphocyte antigen 75); SEQ ID NO: 23 (NTRK2 neurotrophic tyrosine kinase, receptor, type 2); SEQ ID NO: 28 (SCN4B sodium channel, voltage-gated, type IV, beta); and SEQ ID NO: 29 (SFRP1 secreted frizzled-related protein 1). Methods for generating a monoclonal antibody directed against the protein product of one or more of the genes are known to a skilled person. Alternatively, oligoclonics or polyclonal antibodies can be generated using a method known in the art. The generation of oligoclonics is describes in, for example, WO2004009618, WO2004106375, and WO2005068622, which are all three incorporated by reference.

An antibody against one or more of the genes listed in Table 1 can be used as a marker for diagnosing the presence of a breast tumor cell in a breast sample. Furthermore, an antibody against one or more of the genes listed in Table 1 can be used for the preparation of a medicament for treatment of cancer, especially breast cancer. The combination of antibody-mediated treatment with other modalities of cancer immunotherapy is described in, for example, Baxevanis (2008) Expert Opinion on Drug Discovery 3: 441-452, which is incorporated herein by reference.

TABLE 1

Genes used for building of a tumor cell percentage associated profile

| SEQ ID | Sequence | Gene Name | Rank | 13set |
|---|---|---|---|---|
| SEQ ID NO: 1 | CCTGTTCTTCCCCAACTTGGCTTTCCTTTTCTTTTTGGTCATGGGCTCTCAGAGTCTGGG | AI732974 | 7 | yes |
| SEQ ID NO: 2 | GCCCACCTGTCACATCTTTTTGTTTCTTCTATACTGCCTTATTTTGTAGAAAGTAGCTAT | AK025430 | 3 | yes |
| SEQ ID NO: 3 | ATGACATCCCCTCTTGTTTTTGCCTCTCTTTCTCCTGATGCAATGGCCAAAATGCTGAAA | AK094860 | 1 | yes |
| SEQ ID NO: 4 | ACATTCTGAAATCATTTTCTCTGTAAATGGTTGGATTTCATTTCACCCTTAAAGGGATGC | AK125361 | 26 | no |
| SEQ ID NO: 5 | GGCTGTGGTGAAAAAAGCAGAACTACTTAGCAGAGAACAGAAATATGAAGATGGAATTGC | ANAPC7 | 32 | yes |
| SEQ ID NO: 6 | GACCTGAGAACCTGGACCCTGGAATCAGCATGGATGAGACCAGAGGAGGTATGGATGGAA | ANKRD35 | 15 | no |
| SEQ ID NO: 7 | CCTCTGCATATATGTCTCTTTGGAGTTGGAATTTCATTATATGTTAAGAAAATAAAGGAA | AQP1 | 14 | no |
| SEQ ID NO: 8 | AGAGGTCTTAACCTAATGCGCATAGAGAAATTGTTCTCATTGTAAACATACCCCTGTCCT | AY358804 | 17 | no |

TABLE 1-continued

Genes used for building of a tumor cell percentage associated profile

| SEQ ID | Sequence | Gene Name | Rank | 13set |
|---|---|---|---|---|
| SEQ ID NO: 9 | ACCTACCACATTTCCTCCCCACCAAAATAATAATAATAAGGCTACACAGTATCTGGA | BC031974 | 8 | yes |
| SEQ ID NO: 10 | TGGGTGTTTTTGGTTTTTGGTTTCTGGTTTACAATCTCGTCATTCAACAAAGATGGGAG | BC045756 | 16 | no |
| SEQ ID NO: 11 | TCTCAGCACAAGAGCGCTTCCTTTGCACAGAATGAGCTTCGAGCTTTGTTCAGACTAAAT | CBX7 | 19 | no |
| SEQ ID NO: 12 | ACTATATCAAGGACATGAAGGAGAACTGAGTGACCCAGAAGGGGTGGCGAAGGCACAGCT | CCL15 | 34 | no |
| SEQ ID NO: 13 | AGCGAAATTTGAAGATGACATCACCTATTGGCTTAACAGAGATCGAAATGGACATGAATA | ECRG4 | 9 | no |
| SEQ ID NO: 14 | TGCAGCCTCCTTTTCCCTATCTATAAAATAAAAATGACCCTGCTCTATCTCACTGGGCTG | ENST00000300458 | 2 | yes |
| SEQ ID NO: 15 | GTATTGGGGTTCTTGTAGCTTGTTAAAAATTGTCTGCTCCAATCCAGGGTTATTAGGCCA | ENST00000371497 | 5 | no |
| SEQ ID NO: 16 | TCCAGCCGGTCTTTAAAATGAAGATACGTAAAGAAGGGAGAGGTAACTATAGCACAGATC | HEATR3 | 32 | yes |
| SEQ ID NO: 17 | GCCTTGGTGTATGCTATGCTCAGAGGAAAGGCTACTTTTCAAAAGAAACCTCCTTCCAGA | JAM2 | 32 | no |
| SEQ ID NO: 18 | ATACAAAGGTTATTGAAATCTGGGCCTTAAAAGATGAAGAAGATGGAACTCCAGGAAATC | LOC147804 | 18 | yes |
| SEQ ID NO: 19 | TCGCTGCCGACAGAAGTCACTGCCTACCTCAGGGTCCCCTTACCTGGGTGGGAAATAAAT | LOC338328 | 22 | no |
| SEQ ID NO: 20 | TGTGGTTATCACTTTAAGTTTTGACACCTAGATTATAGTCTTAGTAATAGCATCCACTGG | LY75 | 13 | no |
| SEQ ID NO: 21 | TATGGAAGCTGTGAAAATCATCACAAGTGCCTCTGAAAGCGAGTGTTAGGTTGGTTAGAG | METTL7A | 25 | no |
| SEQ ID NO: 22 | GGTAAATGAGAACACTACAACTGTAGTCAGCTCACAATTTTTAAATAAAGGATACCACAG | MYLK | 23 | no |
| SEQ ID NO: 23 | TTCTATACTCTAATCAGCACTGAATTCAGAGGGTTTGACTTTTTCATCTATAACACAGTG | NTRK2 | 6 | no |
| SEQ ID NO: 24 | ATACCCTCACCCTTAAAATTCTCCTGTAACTCAACTAACAAAATCAAGCCTGATTCAAAA | OGT | 11 | yes |
| SEQ ID NO: 25 | GTGGACAAGAAGATGCAGAAGAAAATGAAGAAAGCTCATAAAAAGATGCACAAGCACCAA | PRR13 | 10 | yes |
| SEQ ID NO: 26 | AAGGAGACAAACTCCACCTGGAAATGTTCTGTGAAGGTCAAGTGTGCAAACAGACATTCC | RBP7 | 35 | no |
| SEQ ID NO: 27 | CAATATGCTTGCCACTCCTTAAATGTCCTAATGATGAGAAACTCTCTTTCTGACCAATTG | SCARA5 | 30 | no |
| SEQ ID NO: 28 | ATGCATGGTTTATTCCTCTGGCTTGGATGACAACAATACCCATAGTCAATTTTCCTATGT | SCN4B | 4 | no |
| SEQ ID NO: 29 | CGTTTCCTCTAGTTTCTTCCTGTAGTACTCCTCTTTTAGATCCTAAGTCTCTTACAAAAG | SFRP1 | 27 | no |
| SEQ ID NO: 30 | TCCCAGCCCAACAACAGATTGAAAGAAGCTATAAGTACAAGTAAAGAACAGGAAGCAAAG | SNAP29 | 21 | yes |
| SEQ ID NO: 31 | GAGGCATTGAGAAAGGGGAAAGGCGGGTATTTTTAAAAGCCAAAGATTGACCCAGTTACT | SNF1LK | 12 | no |
| SEQ ID NO: 32 | GACCCTCATCTCTAAAAAGCGAATAAAAACAGAAAAAACACCAAAACAACCAGGATGTCT | TNRC5 | 28 | yes |
| SEQ ID NO: 33 | GAGACAGGTATGAAGGTTTTTGAAAACCGGGCCTTAAAAGATGAAGAAAAGATAGAACTC | TPM3 | 20 | yes |
| SEQ ID NO: 34 | CCCACAAGAGCGTATGCAAATCTCTAAGTTTACGGGACTCTCAATGACCACTATCAGTCA | TSHZ2 | 29 | no |
| SEQ ID NO: 35 | AGTCTTTTGGTGTAATAGTGGGATGTCTGCTTAGTTGGCAGGGGTTCAGTCCAAATGGA | YRDC | 24 | no |

EXAMPLES

Example 1

Materials and Methods

Gene expression analysis of 95 breast tumor samples was performed using custom-made Agilent 44K high-density microarrays. Samples included samples with a low (<30%, 27 samples), medium (30-49, 19 samples) and high (≥50%, 49 samples) tumor cell percentage (TCP).

Figure 1A:
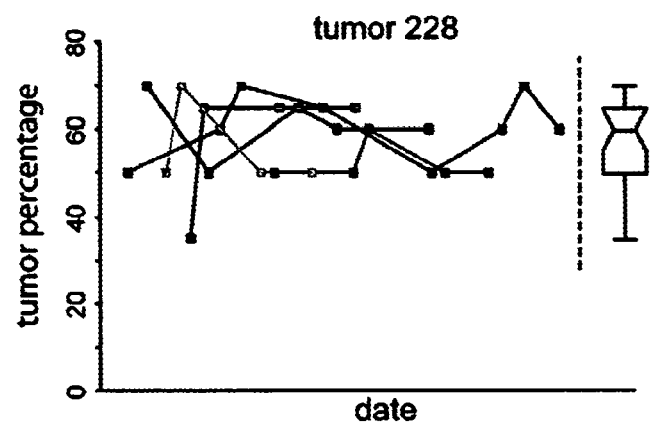
FIG. 1. Variation in histo-pathological tumor percentage scoring. Two HE-colored tumor sections were scored multiple times by five different pathologists (colored lines) during a period of 6 months. Box-plots represent the overall pathological variation in TCP scoring for each of the two tumor samples. (A) Results of histopathological scoring for tumor sample number 228. (B) Results of histopathological scoring for tumor sample number 550.
Figure 1B:
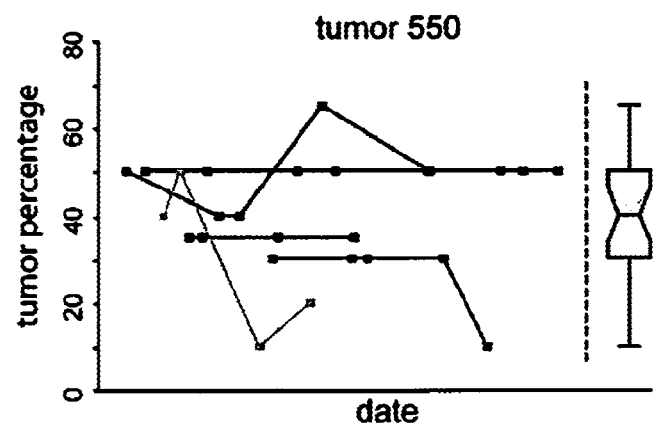

Following data pre-processing and normalization, a supervised learning approach was applied to design a gene expression profile for identification of samples with low and high TCP (training cohort 1). Pathological uncertainly in tumor cell scoring (+/−10%, FIG. 1) was taken into account in the learning model by randomly adjusting the training TCP during each iteration with −10, 0 or 10 percent.

A 3-fold cross validation (CV) method was used to identify a gene expression profile (nearest-mean classifier) that showed a strong association with pathological TCP. This procedure was repeated five-hundred times (multiple sampling approach) and genes were ranked according to their CV performance.

To identify the optimal number of genes to be used in the classifier model, the top ranked gene set was gradually expanded and the classifier performance (area under ROC curve (AUC), leave-one-out CV) was determined for each gene set size.

Next, within the optimal set of 35 top-ranked genes, genes were removed that showed a large variation across an additional set of 70 tumor samples with high (≥50%) TCP (training cohort 2). The remaining set of 13 genes was used to build a nearest-mean classifier and optimal threshold setting and performance on all training samples (165 in total) was determined using a leave-one-out CV. The tumor percentage classifier was validated on 239 independent breast tumor samples.

Results

Figure 2A:
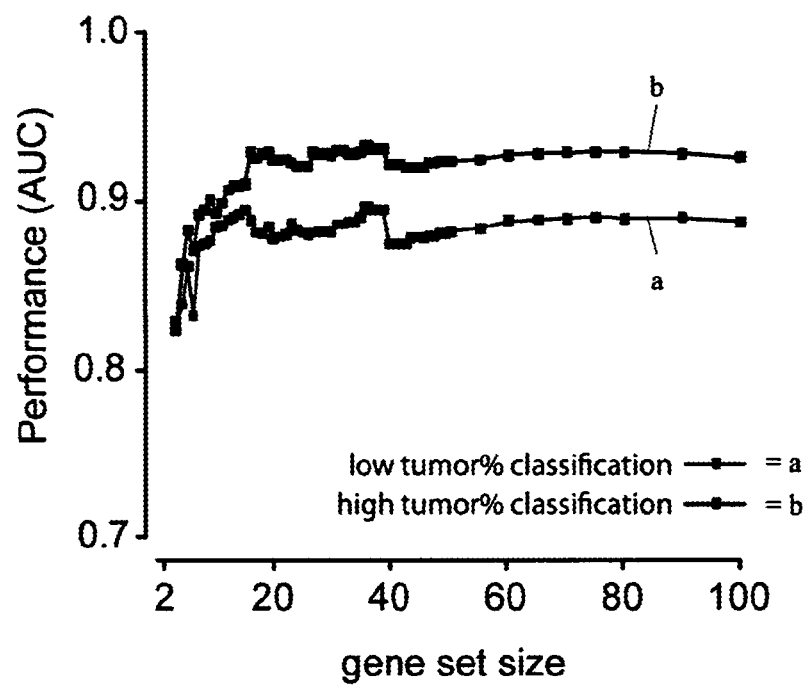
FIG. 2. Identification of a tumor percentage transcriptional profile. (A) Classifier performance (area under ROC curve) using different top-ranked gene set sizes. Performance is given for classification of low (<30%) and high (≥50%) TCP samples. (B) Differential gene expression of top 35 ranked genes between low and high TCP samples. Bars represent expression variation of each gene across 70 high TCP samples. Thirteen most stable differentially expressed genes for high TCP are indicated in blue. (C) Heat-map of the 13-gene tumor percentage profile for 95 training samples. (D) Profile outcome for all 165 training samples. Tumor samples are grouped according to their pathological scoring and ordered according to the profile. Horizontal dashed line represents the optimal classification threshold.

A tumor percentage gene expression profile was identified based on 95 breast tumor samples that ranged in tumor cell content from zero to 85 percent. Multiple sampling 3-fold cross validation (CV) performance indicated a strong association of the selected nearest-mean classifier model with pathological TCP ($R2=0.42$, Wilcoxon P<0.001 [Wilcoxon, 1945. Biometrics Bulletin 1: 80-83; Bauer, 1972. Journal of the American Statistical Association 67, 687-690]). Highest performance of the classifier was reached upon inclusion of the 35 top ranked genes (FIG. 2A), although the performance remained relatively stable for smaller gene set sizes.

Figure 2B:
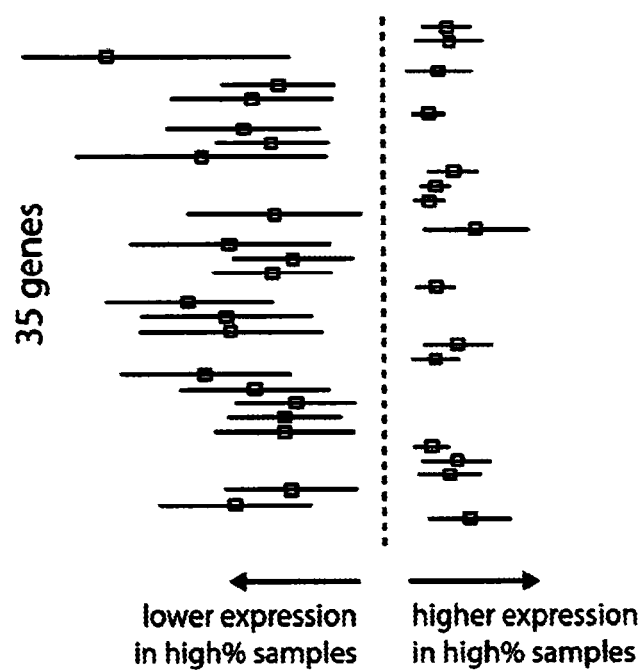
Figure 2C:
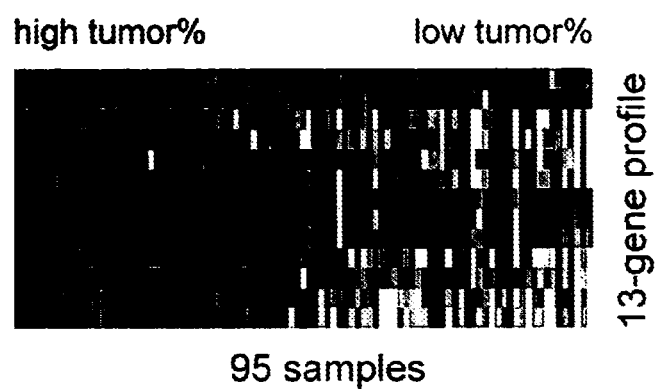

Next, an additional set of 70 tumor samples was used to select within the 35 gene set for genes that showed stable expression in samples with a high tumor percentage. As expected, genes with a higher expression for high TCP (FIG. 2B, right-side) showed a more stable expression across the 70 additional high TCP samples (FIG. 2B, blue bars). The thirteen most stably expressed genes, which were all up-regulated in high versus low TCP (FIG. 2B), were selected to build a robust tumor percentage expression profile (FIG. 2C). The 13-gene classifier showed a high performance (AUC 0.92) for identification of samples that are suitable for, for example, prognosing the tumor sample.

Figure 2D:
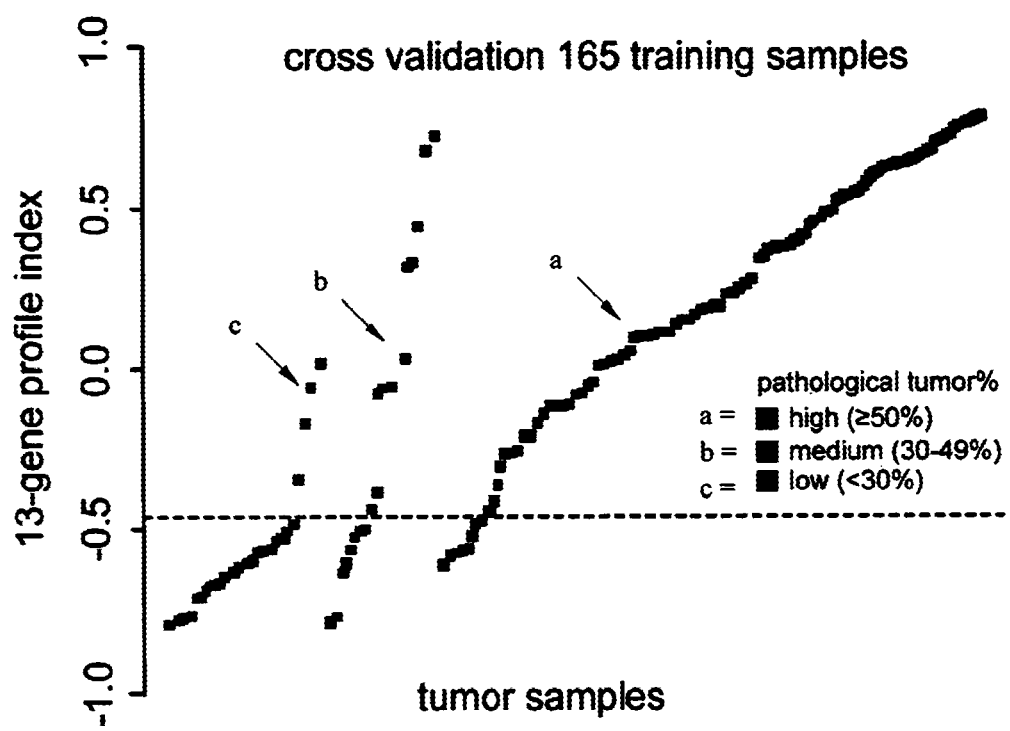

Employment of the optimal classifier threshold for maximum sensitivity and specificity resulted in an accurate classification of 85 percent for low TCP samples and 93 percent for high TCP samples (FIG. 2D).

Figure 3A:
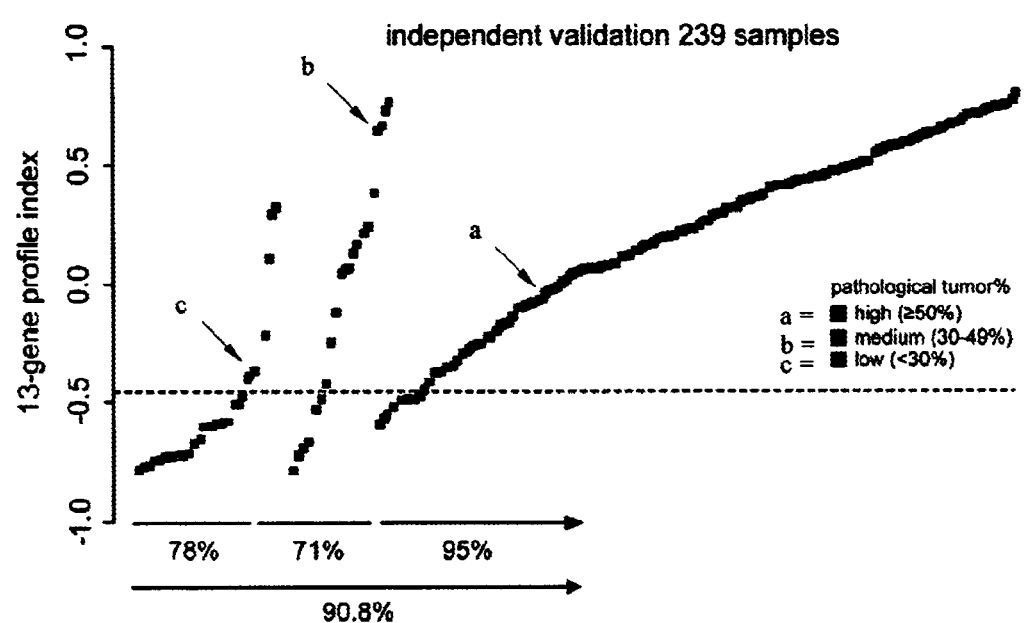
FIG. 3. Validation of the 13-gene tumor percentage profile on 239 independent samples. (A) Profile outcome for 239 independent validation samples. Tumor samples are grouped according to their pathological scoring and ordered according to the profile index. Horizontal line represents the classification threshold that has been determined on the training cohort. (B) Box-plots and statistical differences in profiles indexes between the pathological low, medium and high TCP groups. Colors similar as in A.

The developed tumor percentage profile was validated on an independent set of 239 breast tumor samples. The TCP distribution across this validation cohort was representative for standard diagnostic samples collection. The outcome of the 13-gene profile index was significantly associated with pathological scoring of the validation samples ($R2=0.48$, Wilcoxon P<0.001, AUC 0.90). The molecular classifier correctly assigned 78, 71 and 95 percent of the low, medium and high TCP samples according to the pathological scoring (FIG. 3A) with an overall accuracy of 91 percent and a Kappa score of 0.70 (95% CI 0.54-0.81).

Figure 3B:
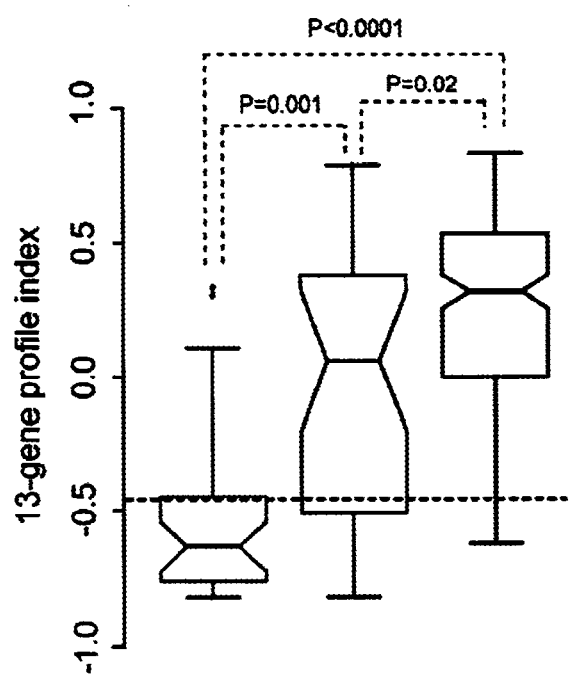

Statistical analysis of the profile indexes indicated a significant difference in outcome between samples with a low and medium TCP (P=0.01, Student's T-test) and between low and high TCP samples (P<0.0001) (FIG. 3B). The difference between medium and high TCP samples is not significant (P=0.02) as the majority of medium TCP samples are correctly classified as high TCP by the molecular profile. The validation results confirm that the molecular profile can accurately discriminate samples with a sufficient tumor percentage for porgnosing the sample based on transcriptional analysis of 13 identified genes.

While gene expression profiles tend to be more robust upon inclusion of a larger set of genes, we decided to limit the developed profile to a relative small number of genes with optimal performance. The rationale behind this strategy is that transcriptional TCP assessment is preferably done before microarray analysis as this assessment will indicate whether a sample is eligible for gene expression profiling.

This approach may prove to be faster and more objective than pathological tumor percentage scoring.

Example 2

To determine the minimal number of signature genes that is needed for an accurate signature, all tumor cell percentage (TCP)-related genes were ranked according to their signature inclusion and their correlation with pathological TCP across 95 training samples (training cohort 1). The top 35 genes represent the identified profile as described.

Figure 4:
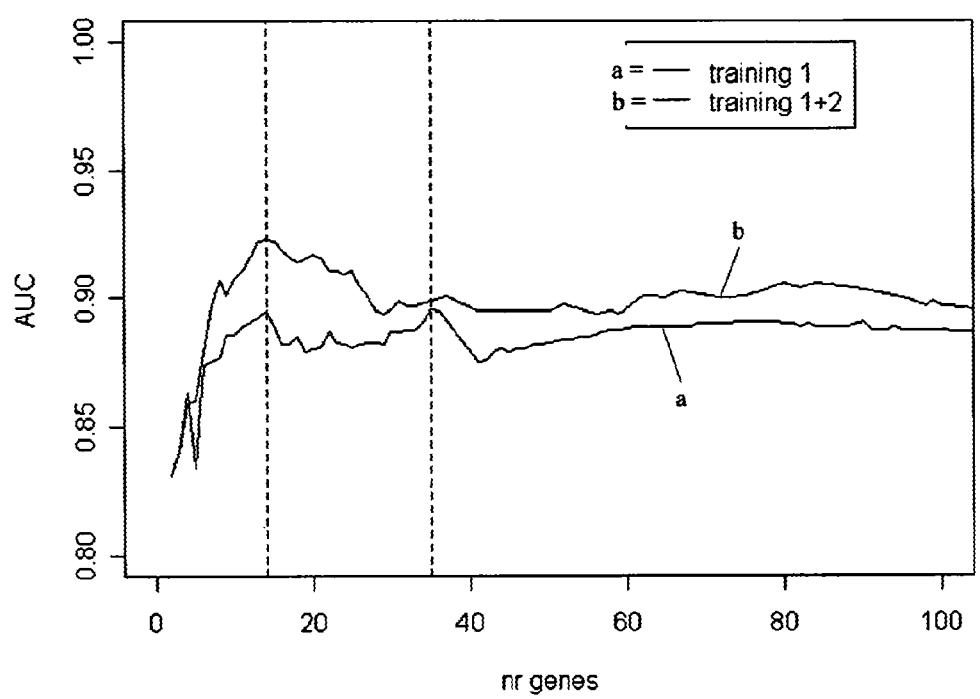
FIG. 4. Performance (AUC) of the TCP nearest mean classifier using different ranked gene set sizes. The black and red lines indicate the classifier performance (AUC, y-axis) based on gene selection using 95 samples (training cohort 1), and using 95 plus 77 samples (training cohorts 1+2) thereby including an additional selection criteria. The horizontal lines represent the optimal selected number of genes: 35 based on training 1, and 13 based on training 1+2 (see example 1 for more details regarding training cohorts).

To investigate a minimal number of top-ranked genes with a significant performance (measured as the area under ROC curve (AUC) which can range from 0.50 (random) to 1.00 (100% accuracy)), we subsequently reduced the set of ranked genes to 2 and calculated the AUC for each gene set size (FIG. 4, black line). The analysis was also performed on ranked gene sets for which the selection procedure included an additional criterion based on a second set of 77 samples (training cohort 2). Results of this second, more robust, gene set analysis are show in red (FIG. 4).

Both analyses result in a high performance for different gene set size with in optimal at 35 and 13 genes. Reduction of the gene set resulted in a slight decrease in accuracy but remained well above 80 percent.

The AUC was also determined for individual genes. It was found that at least SEQ ID NO: 1 (0.88), SEQ ID NO: 2 (0.86), SEQ ID NO: 3 (0.83), SEQ ID NO: (0.81), SEQ ID NO: 9 (0.81), SEQ ID NO: 14 (0.84), SEQ ID NO: 16 (0.87), SEQ ID NO: 18 (0.82), SEQ ID NO: 24 (0.8), SEQ ID NO: 25 (0.80), SEQ ID NO: 30 (0.80), SEQ ID NO: 31 (0.81), SEQ ID NO: 32 (0.79), SEQ ID NO: 33 (0.80), and SEQ ID NO: 35 (0.79) can be used as a single determinant for determining TCP, whereby the determined AUC for each gene is provided within parentheses.

Inclusion of the top 2 genes already resulted in an accuracy of 83 percent and inclusion of the top 10 reached an AUC of 0.89 and 0.91 based on training cohort 1 and 1+2, respectively.

Example 3

Figure 5:
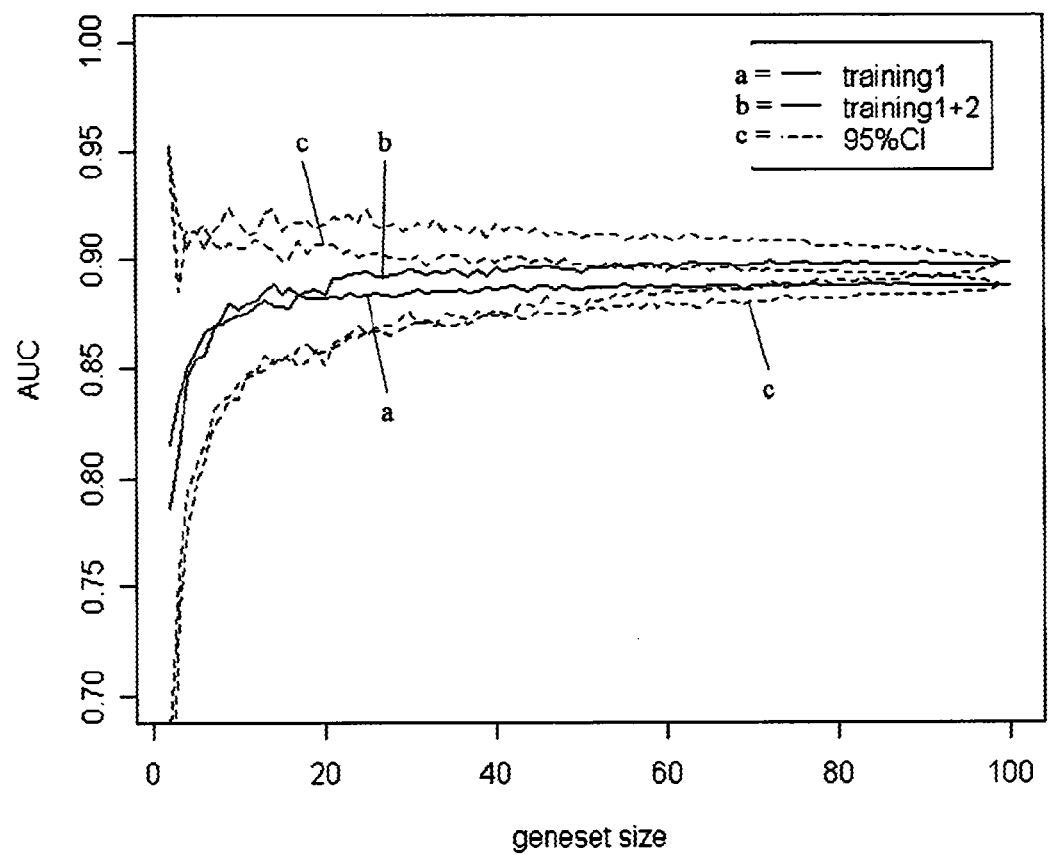
FIG. 5. Performance (AUC) of the TCP nearest mean classifier using random gene sets of different size. TCP classifier performance of random subsets of different size from the total set of 35 genes. For all different subset sizes (2, 3, 4, ... –35) the mean value and 95% confidence interval were calculated for the AUC performance. The black and red lines indicate the classifier performance (AUC, y-axis) based on analysis using 95 samples (training cohort 1), and using 95 plus 77 samples (training cohorts 1+2) thereby including an additional selection criteria (see example 1 for more details regarding training cohorts).

We further analyzed the performance of a random subset of 2 or more genes selected from a larger set of TCP associated genes. All TCP-related genes were ranked according to their signature inclusion and their correlation with pathological TCP across 95 training samples (training cohort 1). We analyzed the performance of a random subset of 2 or more genes selected from the set of 35 genes. Random subsets were selected with different sizes ranging from 2 genes up to all 35 genes. In total, hundred random, computer generated subsets were selected, if possible, for each different gene set size and for each different subset the AUC was calculated. Subsequently, the mean performance and the 95 percent confidence interval were calculated for each different subset size. The data shown in FIG. 5 indicate that random subsets of two or more of the top ranked TCP associated genes show only a marginal drop of the classification performance (FIG. 5). This result confirmed that the performance of the TCP profile does not drop substantially, also in cases when only a small number of genes are used within the prognostic signature. However, the 95% confidence interval of the predictive performances does increase upon use of smaller profile sets. This is explained by the fact that random selection of a small number of genes from the total 100 gene set will result in a much larger variation in prognostic outcome than selection of a large subset. Despite this increase in variation, the performance (AUC) of the TCP profile remains above 0.80 using at least 2 genes and above 0.85 using a minimum of 5 genes. These results indicate that, although the highest performance is achieved using the described set of 13 genes, the use of only 2 genes already results in a TCP profile with significant performance above AUC 0.80.

Example 4

RNA from a tumor sample is hybridized against a breast cancer reference RNA pool using a microarray containing the TCP probes and normalization genes. The reference RNA pool comprises 105 breast cancer samples with a pathological TCP of >50%. Following data pre-processing (local background subtraction, intensity dependent normalization using normalization genes) ratios are calculated between tumor sample and reference. Tumor sample TCP index is determined by calculation of the cosine correlation of the tumor TCP gene expression ratios with the high-TCP profile template and with the low-TCP profile template. If the high-TCP cosine correlation exceeds the low-TCP cosine correlation by a pre-defined factor, the sample will be scored as a high tumor cell percentage samples. If the low-TCP cosine correlation exceeds the high-TCP cosine correlation by a pre-defined factor, it will be scored as a low tumor cell percentage samples. The high-TCP and low-TCP profile templates have been assessed by calculation of the mean gene expression of a cohort of breast tumor samples with at least 50% tumor cell and based on a cohort with less than 30% tumor cells, respectively. This classification procedure is also known as a nearest mean (or centroid) classifier.

The invention claimed is:

1. A method for determining the percentage of tumor cells in a cell sample of an individual, the method comprising
   a. preparing RNA from a cell sample from said individual, said cell sample comprising tumor cells or suspected to comprise tumor cells;
   b. determining RNA levels for a set of genes in said RNA sample; and
   c. determining the percentage of tumor cells in said cell sample on the basis of the levels of RNA determined for the set of genes,
whereby the set of genes comprises genes having SEQ ID NO: 3 and SEQ ID NO: 14, and
   d. selecting a sample for further analyses when the percentage of tumor cells is above a pre-determined threshold.

2. Method according to claim 1, whereby the sample is a sample comprising breast cells of an individual suffering from a breast tumor or suspected of suffering therefrom.

3. Method according to claim 1, wherein determining the percentage of tumor cells in a sample on the basis of RNA levels determined for a set of genes comprises comparing the RNA levels of said set of genes having SEQ ID NO: 3 and SEQ ID NO:14, to the RNA levels of said set of genes in a reference sample.

4. Method according to claim 1, further comprising normalizing the determined RNA levels of the set of genes in the sample.

5. Method according to claim 1, wherein the percentage of tumor cells in a sample of an individual is determined by a set of probes, wherein said probes are specific for genes having SEQ ID NO: 3 and SEQ ID NO: 14.

6. Method according to claim 5, wherein the individual is suffering from a breast tumor or suspected of suffering there from.

7. Method according to claim 1, wherein the percentage of tumor cells in a sample of an individual is determined by a set of primer pairs comprising primer pairs that are specific for genes having SEQ ID NO: 3 and SEQ ID NO: 14.

8. Method according to claim 7, wherein the individual is suffering from a breast tumor or suspected of suffering there from.

9. Method according to claim 1, wherein the percentage of tumor cells in a sample of an individual is determined by determining the level of expression of a set of genes comprising genes having SEQ ID NO: 3 and SEQ ID NO: 14 in a sample of an individual.

10. Method according to claim 9 wherein the individual is suffering from a breast tumor or suspected of suffering therefrom.

11. The method according to claim 9, wherein the method further comprises use of primer pairs that allow the quantitative amplification of said set of genes in the sample.

12. Method of determining a percentage of tumor cells in a sample from an individual suffering from a tumor, or suspected of suffering from a tumor, the method comprising
   classifying a sample as having a tumor cell percentage below or above a defined threshold by a method comprising
      determining a level of RNA for a set of genes comprising genes having SEQ ID NO: 3 and SEQ ID NO: 14 in a sample from said individual;
      determining a similarity value for the level of RNA in the sample and a level of RNA for the set of genes in a patient an individual having no tumor cells; and
      classifying the sample as having a tumor cell percentage above the threshold if said similarity value is below a first similarity threshold value, and classifying said sample as having a tumor cell percentage below the threshold if said similarity value exceeds said first similarity threshold value, and
   selecting a sample for further analyses when the tumor cell percentage is above the threshold.

13. Method according to claim 12, whereby the defined threshold is 30%.

14. Method according to claim 12, whereby the individual is suffering from a breast tumor or suspected of suffering there from.

15. Method according to claim 12, whereby the set of genes comprises SEQ ID NO: 3 and SEQ ID NO: 14.

* * * * *

UNITED STATES PATENT AND TRADEMARK OFFICE
CERTIFICATE OF CORRECTION

| | |
|---|---|
| PATENT NO. | : 8,658,371 B2 |
| APPLICATION NO. | : 13/061286 |
| DATED | : February 25, 2014 |
| INVENTOR(S) | : Paul Roepman and Annuska Maria Glas |

Page 1 of 1

It is certified that error appears in the above-identified patent and that said Letters Patent is hereby corrected as shown below:

IN THE SPECIFICATION:

Column 13, Line 10

Now reads: "SEQ ID NO: (0.81)";
Should read: --SEQ ID NO: 5 (0.81)--

Signed and Sealed this
Sixteenth Day of September, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO. : 8,658,371 B2
APPLICATION NO. : 13/061286
DATED : February 25, 2014
INVENTOR(S) : Roepman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 231 days.

Signed and Sealed this
Fourth Day of August, 2015

Michelle K. Lee
*Director of the United States Patent and Trademark Office*

SEQUENCE LISTING

```
<160> NUMBER OF SEQ ID NOS: 35

<210> SEQ ID NO 1
<211> LENGTH: 60
<212> TYPE: DNA
<213> ORGANISM: Homo sapiens

<400> SEQUENCE: 1
cctgttcttc cccaacttgg ctttcctttt cttttttggtc atgggctctc agagtctggg    60

<210> SEQ ID NO 2
<211> LENGTH: 60
<212> TYPE: DNA
<213> ORGANISM: Homo sapiens

<400> SEQUENCE: 2
gcccacctgt cacatctttt tgtttcttct atactgcctt attttgtaga aagtagctat    60

<210> SEQ ID NO 3
<211> LENGTH: 60
<212> TYPE: DNA
<213> ORGANISM: Homo sapiens
```

<400> SEQUENCE: 3
atgacatccc ctcttgtttt tgcctctctt tctcctgatg caatggccaa aatgctggaa    60

<210> SEQ ID NO 4
<211> LENGTH: 60
<212> TYPE: DNA
<213> ORGANISM: Homo sapiens

<400> SEQUENCE: 4
acattctgaa atcattttct ctgtaaatgg ttggatttca tttcaccctt aaagggatgc    60

<210> SEQ ID NO 5
<211> LENGTH: 60
<212> TYPE: DNA
<213> ORGANISM: Homo sapiens

<400> SEQUENCE: 5
ggctgtggtg aaaaaagcag aactacttag cagagaacag aaatatgaag atggaattgc    60

<210> SEQ ID NO 6
<211> LENGTH: 60
<212> TYPE: DNA
<213> ORGANISM: Homo sapiens

<400> SEQUENCE: 6
gacctgagaa cctggaccct ggaatcagca tggatgagac cagaggaggt atggatggaa    60

<210> SEQ ID NO 7
<211> LENGTH: 60
<212> TYPE: DNA
<213> ORGANISM: Homo sapiens

<400> SEQUENCE: 7
cctctgcata tatgtctctt tggagttgga atttcattat atgttaagaa aataaaggaa    60

<210> SEQ ID NO 8
<211> LENGTH: 60
<212> TYPE: DNA
<213> ORGANISM: Homo sapiens

<400> SEQUENCE: 8
agaggtctta acctaatgcg catagagaaa ttgttctcat tgtaaacata ccctgtcct    60

<210> SEQ ID NO 9
<211> LENGTH: 60
<212> TYPE: DNA
<213> ORGANISM: Homo sapiens

<400> SEQUENCE: 9
acctaccaca tttcctcccc accaaaataa taataataat aaggctacac agtatctgga    60

<210> SEQ ID NO 10
<211> LENGTH: 60
<212> TYPE: DNA
<213> ORGANISM: Homo sapiens

<400> SEQUENCE: 10
tgggtgtttt ttggtttttg gtttctggtt tacaatctcg tcattcaaca aagatgggag    60

<210> SEQ ID NO 11
<211> LENGTH: 60
<212> TYPE: DNA

```
<400> SEQUENCE: 11
tctcagcaca agagcgcttc ctttgcacag aatgagcttc gagctttgtt cagactaaat    60

<210> SEQ ID NO 12
<211> LENGTH: 60
<212> TYPE: DNA
<213> ORGANISM: Homo sapiens

<400> SEQUENCE: 12
actatatcaa ggacatgaag gagaactgag tgacccagaa ggggtggcga aggcacagct    60

<210> SEQ ID NO 13
<211> LENGTH: 60
<212> TYPE: DNA
<213> ORGANISM: Homo sapiens

<400> SEQUENCE: 13
agcgaaattt gaagatgaca tcacctattg gcttaacaga gatcgaaatg gacatgaata    60

<210> SEQ ID NO 14
<211> LENGTH: 60
<212> TYPE: DNA
<213> ORGANISM: Homo sapiens

<400> SEQUENCE: 14
tgcagcctcc ttttccctat ctataaaata aaaatgaccc tgctctatct cactgggctg    60

<210> SEQ ID NO 15
<211> LENGTH: 60
<212> TYPE: DNA
<213> ORGANISM: Homo sapiens

<400> SEQUENCE: 15
gtattggggt tcttgtagct tgttaaaaat tgtctgctcc aatccagggt tattaggcca    60

<210> SEQ ID NO 16
<211> LENGTH: 60
<212> TYPE: DNA
<213> ORGANISM: Homo sapiens

<400> SEQUENCE: 16
tccagccggt ctttaaaatg aagatacgta aagaagggag aggtaactat agcacagatc    60

<210> SEQ ID NO 17
<211> LENGTH: 60
<212> TYPE: DNA
<213> ORGANISM: Homo sapiens

<400> SEQUENCE: 17
gccttggtgt atgctatgct cagaggaaag gctacttttc aaaagaaacc tccttccaga    60

<210> SEQ ID NO 18
<211> LENGTH: 60
<212> TYPE: DNA
<213> ORGANISM: Homo sapiens

<400> SEQUENCE: 18
atacaaaggt tattgaaatc tgggccttaa aagatgaaga agatggaact ccaggaaatc    60

<210> SEQ ID NO 19
<211> LENGTH: 60
<212> TYPE: DNA
<213> ORGANISM: Homo sapiens
```

```
<400> SEQUENCE: 19
tcgctgccga cagaagtcac tgcctacctc agggtcccct tacctgggtg ggaaataaat    60

<210> SEQ ID NO 20
<211> LENGTH: 60
<212> TYPE: DNA
<213> ORGANISM: Homo sapiens

<400> SEQUENCE: 20
tgtggttatc actttaagtt ttgacaccta gattatagtc ttagtaatag catccactgg    60

<210> SEQ ID NO 21
<211> LENGTH: 60
<212> TYPE: DNA
<213> ORGANISM: Homo sapiens

<400> SEQUENCE: 21
tatggaagct gtgaaaatca tcacaagtgc ctctgaaagc gagtgttagg ttggttagag    60

<210> SEQ ID NO 22
<211> LENGTH: 60
<212> TYPE: DNA
<213> ORGANISM: Homo sapiens

<400> SEQUENCE: 22
ggtaaatgag aacactacaa ctgtagtcag ctcacaattt ttaaataaag gataccacag    60

<210> SEQ ID NO 23
<211> LENGTH: 60
<212> TYPE: DNA
<213> ORGANISM: Homo sapiens

<400> SEQUENCE: 23
ttctatactc taatcagcac tgaattcaga gggtttgact ttttcatcta taacacagtg    60

<210> SEQ ID NO 24
<211> LENGTH: 60
<212> TYPE: DNA
<213> ORGANISM: Homo sapiens

<400> SEQUENCE: 24
ataccctcac ccttaaaatt ctcctgtaac tcaactaaca aaatcaagcc tgattcaaaa    60

<210> SEQ ID NO 25
<211> LENGTH: 60
<212> TYPE: DNA
<213> ORGANISM: Homo sapiens

<400> SEQUENCE: 25
gtggacaaga agatgcagaa gaaaatgaag aaagctcata aaaagatgca caagcaccaa    60

<210> SEQ ID NO 26
<211> LENGTH: 60
<212> TYPE: DNA
<213> ORGANISM: Homo sapiens

<400> SEQUENCE: 26
aaggagacaa actccacctg gaaatgttct gtgaaggtca agtgtgcaaa cagacattcc    60

<210> SEQ ID NO 27
<211> LENGTH: 60
<212> TYPE: DNA
<213> ORGANISM: Homo sapiens
```

```
<400> SEQUENCE: 27
caatatgctt gccactcctt aaatgtccta atgatgagaa actctctttc tgaccaattg    60

<210> SEQ ID NO 28
<211> LENGTH: 60
<212> TYPE: DNA
<213> ORGANISM: Homo sapiens

<400> SEQUENCE: 28
atgcatggtt tattcctctg gcttggatga caacaatacc catagtcaat tttcctatgt    60

<210> SEQ ID NO 29
<211> LENGTH: 60
<212> TYPE: DNA
<213> ORGANISM: Homo sapiens

<400> SEQUENCE: 29
cgtttcctct agtttcttcc tgtagtactc ctcttttaga tcctaagtct cttacaaaag    60

<210> SEQ ID NO 30
<211> LENGTH: 60
<212> TYPE: DNA
<213> ORGANISM: Homo sapiens

<400> SEQUENCE: 30
tcccagccca acaacagatt gaaagaagct ataagtacaa gtaaagaaca ggaagcaaag    60

<210> SEQ ID NO 31
<211> LENGTH: 60
<212> TYPE: DNA
<213> ORGANISM: Homo sapiens

<400> SEQUENCE: 31
gaggcattga gaaaggggaa aggcgggtat ttttaaaagc caaagattga cccagttact    60

<210> SEQ ID NO 32
<211> LENGTH: 60
<212> TYPE: DNA
<213> ORGANISM: Homo sapiens

<400> SEQUENCE: 32
gaccctcatc tctaaaaagc gaataaaaac agaaaaaaca ccaaaacaac caggatgtct    60

<210> SEQ ID NO 33
<211> LENGTH: 60
<212> TYPE: DNA
<213> ORGANISM: Homo sapiens

<400> SEQUENCE: 33
gagacaggta tgaaggtttt tgaaaaccgg gccttaaaag atgaagaaaa gatagaactc    60

<210> SEQ ID NO 34
<211> LENGTH: 60
<212> TYPE: DNA
<213> ORGANISM: Homo sapiens

<400> SEQUENCE: 34
cccacaagag cgtatgcaaa tctctaagtt tacgggactc tcaatgacca ctatcagtca    60
```

```
<210> SEQ ID NO 35
<211> LENGTH: 60
<212> TYPE: DNA
<213> ORGANISM: Homo sapiens

<400> SEQUENCE: 35 agtcttttg gtgtaatagt gggatgtctg cttagttggc aggggttcag tccaaatgga    60
```